United States Patent [19]
Peri et al.

[11] Patent Number: 5,955,575
[45] Date of Patent: Sep. 21, 1999

[54] ANTAGONISTS OF G-PROTEIN-COUPLED RECEPTOR

[75] Inventors: Krishna G. Peri; Sylvain Chemtob; Michel Potier, all of Montreal, Canada

[73] Assignee: Hôpital Sainte-Justine, Montréal, Canada

[21] Appl. No.: 08/995,927

[22] Filed: Dec. 22, 1997

[51] Int. Cl.$^6$ .......................... A61K 38/04; A61K 38/16
[52] U.S. Cl. .......................... 530/324; 530/326; 514/12; 514/13; 514/14
[58] Field of Search ...................................... 530/324, 326

[56] References Cited

PUBLICATIONS

Database Embase, AN 85040376. Jakobs, K.et al. J. Recept. Res. 4, 443–458, Jan. 1984.
Lameh J. et al. Pharmaceutical Research, 7, 1213–1221, Dec. 1990.
Abramovitz, M., Boie, Y., Nguyen, T., Rushmore, T.H., Bayne, M.A., Metters, K.M., Slipetz, D.M., and Grygorczyk, R. 1994. Cloning and expression of a cDNA for the human prostanoid FP receptor. J. Biol. Chem. 269: 2632–2636.
Berridge, M.J., Dawson, R.C.M., Downes, P.C., Heslop, J.P., and Irvine, R.F. 1983. Changes in the levels of inositol phosphates after agonist–dependent hydrolysis of membrane phosphoinositides. Biochem. J. 212: 473–482.
Chomczynski, P., and Sacchi, N. 1987. Single–step method of RNA isolation by acid guanidinium thiocyanate–phenol–chloroform extraction. Anal. Biochem. 162: 156–159.
Johnson, J. A., Gray, M.O., Karliner, J.S. Chen, C.H., and Mochly–Rosen, D. 1996. An improved permeabilization protocol for the introduction of peptides into cardiac myocytes: application to protein kinase C research. Circ. Res. 79: 10086–1099.
Lambright, D.G., Sondek, J., Bohm, A., Skiba, N.P., Hamm, H.E. and Sigler, P.B. 1996. The 2.0 Å crystal structure of a heterotrimeric G protein. Nature. 379: 311–319.
Peri, K.G., Hardy, P., Li. D.Y., Varma, D.R., and Chemtob, S.C. 1995. Prostaglandin G/H synthase–2 is a major contributor of brain prostaglandins in the newborn. J. Biol. chem. 270: 24615–24620.
Strader, C.D., Fong, T.M., Tota, M.R., and Underwood, D. 1994. Structure and function of G–protein coupled receptors. Ann. Rev. Biochem. 63: 101–132.
Sugimoto, Y., Yamasaki, A., Segi, E., Tsuboi, K., Aze, Y., Nishimura, T., Oida, H., Yoshida, N., Tanaka, T., Katsuyama, M., Hasumoto, K., Murata, T., Hirata, M., Ushikubi, F., Negishi, M., Ichikawa, A., and Narumiya S. 1997. Failure of parturition in mice lacking the prostaglandin F receptor. Science. 277: 81–83.

*Primary Examiner*—Cecilia J. Tsang
*Assistant Examiner*—Michael Borin
*Attorney, Agent, or Firm*—Swabey Ogilvy Renault; France Côté

[57] ABSTRACT

The present invention relates to a new class of G-protein-coupled receptor antagonists which bind to the intracellular molecular interface between the receptor and the G-protein, thus hampering signal transduction. The present invention describes peptide sequences derived from the prostaglandin receptor $F_{2\alpha}$ and the G-protein, G$\alpha$q protein, produced by molecular biology techniques or chemical synthesis, as selective inhibitors of signal transduction involved in the stimulation of this receptor. Such peptides or molecules derived from their primary, secondary and tertiary structures may be used as effective tocolytics for the prevention of premature labor or be utilized for the treatment of dysmenorrhea.

2 Claims, 2 Drawing Sheets

SEQUENCE LISTING

<160> NUMBER OF SEQ ID NOS: 10

<210> SEQ ID NO 1
<211> LENGTH: 57
<212> TYPE: DNA
<213> ORGANISM: Artificial Sequence
<220> FEATURE:
<223> OTHER INFORMATION: DNA fragments encoding the intracellular domain
      of the FP receptor

<400> SEQUENCE: 1
agagttaaat ttaaaagtca gcagcacaga caaggcagat ctcatcattt ggaaatg          57

<210> SEQ ID NO 2
<211> LENGTH: 156
<212> TYPE: DNA
<213> ORGANISM: Artificial Sequence
<220> FEATURE:
<223> OTHER INFORMATION: DNA fragments encoding the intracellular domain
      of the FP receptor

<400> SEQUENCE: 2
cgaaaggctg tccttaagaa tctctataag cttgccagtc aatgctgtgg agtgcatgtc       60
atcagcttac atatttggga gcttagttcc attaaaaatt ccttaaaggt tgctgctatt     120
tctgagtcac cagttgcaga gaaatcagca agcacc                                156

<210> SEQ ID NO 3
<211> LENGTH: 19
<212> TYPE: PRT
<213> ORGANISM: Artificial Sequence
<220> FEATURE:
<223> OTHER INFORMATION: Peptide for use as antagonists of
      G-protein-coupled receptor

<400> SEQUENCE: 3

Arg Val Lys Phe Lys Ser Gln Gln His Arg Gln Gly Arg Ser His His
1               5                   10                  15

Leu Glu Met

<210> SEQ ID NO 4
<211> LENGTH: 52
<212> TYPE: PRT
<213> ORGANISM: Artificial Sequence
<220> FEATURE:
<223> OTHER INFORMATION: Peptide for use as antagonists of
      G-protein-coupled receptor

<400> SEQUENCE: 4

Arg Lys Ala Val Leu Lys Asn Leu Tyr Lys Leu Ala Ser Gln Cys Cys
1               5                   10                  15

Gly Val His Val Ile Ser Leu His Ile Trp Glu Leu Ser Ser Ile Lys
            20                  25                  30

Asn Ser Leu Lys Val Ala Ala Ile Ser Glu Ser Pro Val Ala Glu Lys
        35                  40                  45

Ser Ala Ser Thr
    50

<210> SEQ ID NO 5
<211> LENGTH: 33
<212> TYPE: DNA
<213> ORGANISM: Artificial Sequence
<220> FEATURE:
<223> OTHER INFORMATION: primer for reverse transcripting the human FP receptor

<400> SEQUENCE: 5
gcgtctagaa tgagagttaa atttaaaagt cag                                33

<210> SEQ ID NO 6
<211> LENGTH: 27
<212> TYPE: DNA
<213> ORGANISM: Artificial Sequence
<220> FEATURE:
<223> OTHER INFORMATION: primer for reverse transcripting the human FP
      receptor

<400> SEQUENCE: 6
gcgtctagac tacatttcca aatgatg                                       27

<210> SEQ ID NO 7
<211> LENGTH: 30
<212> TYPE: DNA
<213> ORGANISM: Artificial Sequence
<220> FEATURE:
<223> OTHER INFORMATION: primer for reverse transcripting the human FP
      receptor

<400> SEQUENCE: 7
cgctctagaa tgcgaaaggc tgtccttaag                                    30

<210> SEQ ID NO 8
<211> LENGTH: 30
<212> TYPE: DNA
<213> ORGANISM: Artificial Sequence
<220> FEATURE:
<223> OTHER INFORMATION: primer for reverse transcripting the human FP
      receptor

<400> SEQUENCE: 8
gcgtctgagc taggtgcttg ctgatttctc                                    30

<210> SEQ ID NO 9
<211> LENGTH: 30
<212> TYPE: PRT
<213> ORGANISM: Artificial Sequence
<220> FEATURE:
<223> OTHER INFORMATION: Peptide for use as antagonists of
      G-protein-coupled receptor

<400> SEQUENCE: 9

Cys Leu Ser Glu Glu Ala Lys Glu Ala Arg Arg Ile Asn Asp Glu Ile
 1               5                  10                  15

Glu Arg Gln Leu Arg Arg Asp Lys Arg Asp Ala Arg Arg Glu
            20                  25                  30

<210> SEQ ID NO 10
<211> LENGTH: 15
<212> TYPE: PRT
<213> ORGANISM: Artificial Sequence
<220> FEATURE:
<223> OTHER INFORMATION: Peptide for use as antagonists of
      G-protein-coupled receptor

<400> SEQUENCE: 10

Lys Asp Thr Ile Leu Gln Leu Asn Leu Lys Glu Tyr Asn Leu Val
 1               5                  10                  15

ANTAGONISTS OF G-PROTEIN-COUPLED RECEPTOR

BACKGROUND OF THE INVENTION (a) Field of the Invention

The invention relates to G-protein-coupled receptor antagonists which bind to the intracellular molecular interface between the receptor for $PGF_{2\alpha}$ (FP receptor) and the G-protein.

(b) Description of Prior Art

Prostaglandins are derived from the oxygenation of arachidonic acid by prostaglandin synthases. Prostaglandins mediate a wide variety of physiological actions, such as vasomotricity, sleep/wake cycle, intestinal secretion, lipolysis, glomelular filtration, mast cell degranulation, neurotransmission, platelet aggregation, leuteolysis, myometrial contraction and labor, inflammation and arthritis, patent ductus arteriosus, cell growth and differentiation. Prostanoids mediate their actions through binding to distinct receptors which belong to the super family of rhodopsin-like seven transmembrane helical receptors. These receptors are coupled to heterotrimeric G-proteins consisting of $\alpha$, $\beta$ and $\gamma$ subunits which, upon activation, elicit alterations in cell calcium, initiate phosphoinositide hydrolysis or promotion or repression of cyclic adenosine monophosphate synthesis (Strader, C. D., et al., *Ann. Rev. Biochem.* 63: 101–132, 1994).

Of the five pharmacologically distinct prostanoid receptors for $E_2$, $I_2$, $D_2$, $TxA_2$ and $F_{2\alpha}$ and their many isoforms, the receptor for $PGF_{2\alpha}$, also called FP receptor, shows limited tissue distribution, predominantly expressed in corpora leutea, uterine myometrium, trabecular meshwork of the eye, and to a lesser extent in vascular smooth muscle. Initiation of labor is marked by tremendous rise in $PGF_{2\alpha}$ levels and increased uterine contractility. The wide spread use of $PGF_{2\alpha}$ analogues to induce labor in veterinary industry points to the primary role of $PGF_{2\alpha}$ and its receptor in parturition. This is underscored by the fact that mice lacking the FP receptor fail to undergo labor (Sugimoto, Y., et al., *Science*, 277: 81–83, 1997).

In face of escalating costs incurred as a result of premature births and associated complications to the neonate, such as intraventricular hemorrhage, bronchopulmonary displasia and periventricular leukomalacia leading to cerebral palsy, prolongation of gestation by arresting premature labor is an effective preventive therapy. The relative success of nonsteroidal anti-inflammatory drugs as a short term therapy toward prevention of premature labor is based on their inhibitory actions upon the synthesis of prostaglandins, particularly $PGE_2$ and $PGF_{2\alpha}$. However, inhibition of the former is associated with serious complications to the fetus such as the closure of ductus arteriosus, renal failure and pulmonary hypertension. At another level, $PGF_{2\alpha}$ has been attributed a major role in dysmenorrhea, a condition which afflicts 5%–7% of premenopausal women. A premenstrual increase in $PGF_{2\alpha}$ levels resulting in myometrial spasms underlies the pathogenesis of this disorder. Lack of effective antagonists of FP receptor for extended therapy hampered the advances in preventing premature labor and associated sequelae.

Human FP receptor is a 45 kDa integral membrane glycoprotein, consisting of 359 amino acids and shares only 47% sequence identity with EP1 receptor, and to a lesser extent with other prostanoid receptors (Abramovitz, M., et al., *J. Biol. Chem.*, 269: 2632–2636., 1994). Binding of $PGF_{2\alpha}$ to FP receptor is followed by the activation of $G_{60\ q\beta\gamma}$ complex, increased GTP binding by the $G_{\alpha q}$ subunit, stimulation of phospholipase $\beta$ activity, release of inositol phosphates, increased intracellular calcium and subsequent signal transduction phenomena ultimately leading to smooth muscle contraction. The FP receptor is the only efficacious target for development of therapeutic drugs since a few $G_{60}$-proteins catalyze the actions of hundreds of G-protein coupled receptors, thus targets downstream from the receptor are essentially of little use.

Antagonists of FP receptors directed to the ligand binding site could be of limited use since ligand based inhibitors show cross reactivity with other prostanoid receptors; their efficacy will be compromised in face of tremendous increase in $PGF_{2\alpha}$ concentrations in myometrium at the onset of labor; and the basal activity of the receptors in the absence of ligand limits the use of ligand-based inhibitors.

It would be highly desirable to be provided with antagonists of FP receptors which do not cross-react with other prostanoid receptors and which are effective even in the absence of a ligand.

SUMMARY OF THE INVENTION

One aim of the present invention is to provide antagonists of FP receptors which do not cross-react with other prostanoid receptors and which are effective even in the absence of a ligand.

Another aim of the present invention is to provide inhibitors of FP receptors devised by a novel strategy to target the intracellular surface of the receptor at which the cytoplasmic domains of the FP receptor and the $G_q$ protein interact.

In accordance with the present invention there is provided a G-protein-coupled receptor antagonist which binds to an intracellular molecular interface between a receptor and a G-protein, wherein the antagonist when bound to the intracellular molecular interface hamper the transduction of a signal.

The receptor is preferably the FP receptor of prostaglandin.

The antagonist of the present invention preferably comprises an amino acid sequence derived from the sequence of at least one of the prostaglandin $F_{2\alpha}$ receptor and the associated protein $G_{\alpha q}$.

In accordance with the present invention there is also provided a method for preventing premature delivery of fetus comprising the step of administering to a female in need of such a treatment a therapeutically effective amount of a G-protein-coupled receptor antagonist which binds to an intracellular molecular interface between a receptor and a G-protein, wherein the antagonist when bound to the intracellular molecular interface hamper the transduction of a signal, thereby reducing contractions.

In accordance with the present invention there is also provided a method for preventing and/or treating dysmenorrhea comprising the step of administering to a female in need of such a treatment a therapeutically effective amount of a G-protein-coupled receptor antagonist which binds to an intracellular molecular interface between a receptor and a G-protein, wherein the antagonist when bound to the intracellular molecular interface hamper the transduction of a signal thereby reducing pain associated with contractions.

DETAILED DESCRIPTION OF THE INVENTION

Figure 1A:
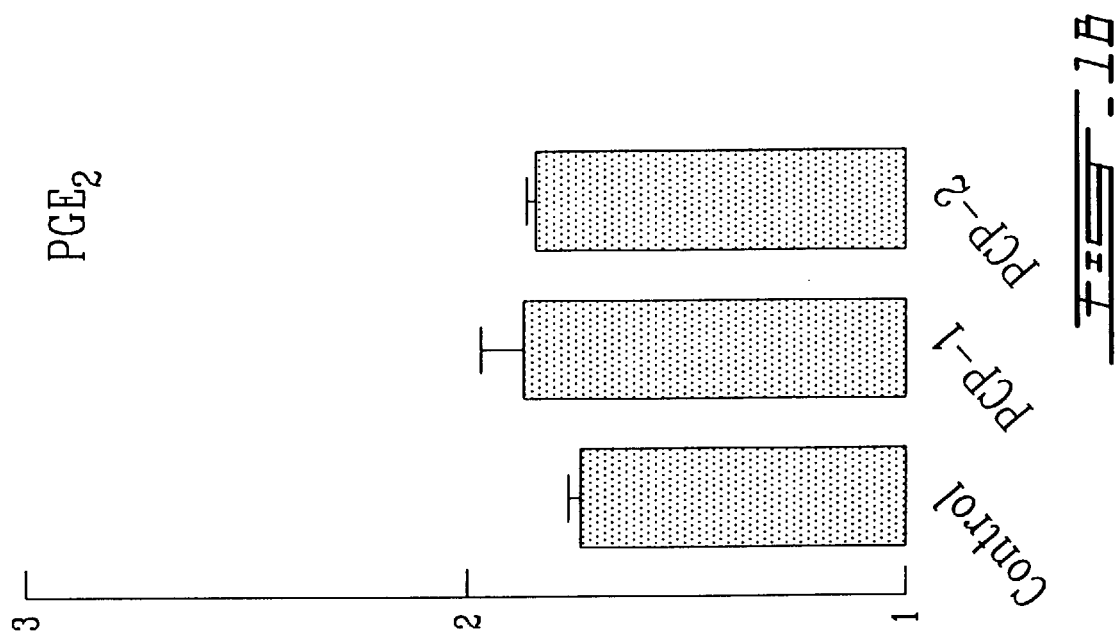
FIGS. 1A and 1B illustrate the inhibitory effects of PCP-1 and PCP-2 on FP receptor function upon stimulation with $PGF_{2\alpha}$ or $PGE_2$ in accordance with one embodiment of the present invention.

In accordance with the present invention, there is provided a new class of G-protein-coupled receptor antagonists which bind to the intracellular molecular interface between the receptor and the G-protein, thus hampering signal transduction.

Hence, a novel strategy to target the intracellular surface of the receptor at which the cytoplasmic domains of FP receptor and Gq protein interact was designed. By preventing the binding of Gq protein to FP receptor with the inhibitors of the present invention, derived from both the FP receptor and Gq protein, FP receptor function in the presence of its ligand was diminished. Furthermore, the specificity of the inhibitors of the present invention is demonstrated by analyzing the function of a highly related prostaglandin receptor, EP1.

PREPARATION OF INHIBITORS

Cell Culture

A549 lung carcinoma cells (ATCC Accession No.: CCL185, American Type Culture Collection, Rockville, Md. 20852), were cultured in Dulbecco's modified Eagles medium (DMEM) with 10% fetal bovine serum (FBS) and antibiotics, penicillin (10 U/ml) and streptomycin (10 µg/ml) in a humidified atmosphere containing 5% $CO_2$ at 37° C. The cells were trypsinized and plated in 6-well tissue culture dishes at $2\times10^5$ cells/well, a day before commencing the experiments.

Cloning FP receptor intracellular domains

The DNA fragments 5' AGA GTT AAA TTT AAA AGT CAG CAG CAC AGA CAA GGC AGA TCT CAT CAT TTG GAA ATG 3' (SEQ ID NO: 1) and 5' CGA AAG GCT GTC CTT AAG AAT CTC TAT AAG CTT GCC AGT CAA TGC TGT GGA GTG CAT GTC ATC AGC TTA CAT ATT TGG GAG CTT AGT TCC ATT AAA AAT TCC TTA AAG GTT GCT GCT ATT TCT GAG TCA CCA GTT GCA GAG AAA TCA GCA AGC ACC 3' (SEQ ID NO: 2), encoding the intracellular domains of the FP receptor having the following amino acid sequences: RVKFKSQQHR QGRSHHLEM (PCP-1) (SEQ ID NO: 3) and RKAVLKNLYK LASQC-CGVHV ISLHIWELSS IKNSLKVAAI SESPVAEKSA ST (PCP-2) (SEQ ID NO: 4) were cloned by RT-PCR. Total mRNA from human foreskin fibroblasts were prepared by acid phenol-guanidine isothiocyanate method (Chomczynski, P., and Sacchi, N., *Anal. Biochem.*, 162: 156–159, 1987).

Reverse transcription followed by amplification of the cDNAs using the gene-specific primers pcp 1.1: 5' GCG TCT AGA ATG AGA GTT AAA TTT AAA AGT CAG 3' (SEQ ID NO: 5), pcp 1.2: 5' GCG TCT AGA CTA CAT TTC CAA ATG ATG 3' (SEQ ID NO: 6) pcp 2.1: 5' CGC TCT AGA ATG CGA AAG GCT GTC CTT AAG 3' (SEQ ID NO: 7) amd pcp 2.2: 5' GCG TCT GAG CTA GGT GCT TGC TGA TTT CTC 3' (SEQ OD NO: 8), derived from the human FP receptor sequence (Abramovitz, M., et al., *J. Biol. Chem.*, 269: 2632–2636, 1994) and Taq™ polymerase (GIBCO Life Technologies, Burlington, ON) were conducted as described by Peri et al. (Peri, K. G., et al., *J. Biol. chem.*, 270: 24615–24620, 1995). Briefly, two micrograms of total RNA was reverse transcribed using 400 U of M-MLV reverse transcriptase and 10 µg/ml random hexamers, in a 50 µl reaction containing 50 mM Tris-HCl, pH 8.3, 75 mM KCl, 3 mM $MgCl_2$, 10 mM DTT, and 0.5 mM each of dCTP, dGTP, dATP and dTTP, for 1 h, at 42° C. An aliquot of the CDNA (equivalent to 1 µg of RNA) was amplified using 1.5 U Taq DNA polymerase in a 100 µl reaction buffer containing 20 mM Tris-HCl, pH 8.4, 50 mM KCl 1.5 mM $MgCl_2$, 0.2 mM each of dCTP, dGTP, DATP and dTTP, and 0.5 µM each of the primers, for 35 cycles (each cycle was 94° C., 1 min.; 50° C., 1 min.; and 72° C., 1 min.).

The PCR products were digested with Xba I restriction enzyme (GIBCO Life Technologies, Burlington, ON) and cloned into the Xba I site of pRC-CMV vector (Invitrogen, Calif.). Multiple plasmid clones were sequenced using the T7 sequencing kit (Pharmacia, Baie D'Urfe, PQ) to verify the sequence of the cDNAs.

Cell transfection and selection of G418-resistant clones

The expression plasmids carrying the third (PCP-1) and the fourth (PCP-2) intracellular domains were introduced into A549 cells using Transfectamine lipid (GIBCO Life Technologies, Burlington, ON). Three (3) micrograms of DNA and 16 µg of lipid were mixed in 200 µl of water and incubated at room temperature for 45 min. Then, the lipid-DNA complexes were diluted with 0.8 ml of Opti-MEM™ (GIBCO Life Technologies, Burlington, ON). The cells were washed twice with Hank's Balanced Salt Solution and incubated with lipid-DNA complexes for 6 hours. An equal volume of DMEM with 20% FBS was added and the cells were kept in the incubator overnight. On the next day, the medium was replaced with DMEM containing 10% FBS and antibiotics and incubated for another 24 hours.

On the following day, the cells were trypsinized and plated in 100 mm cell culture dishes at $1\times10^4$ cells/ml in DMEM containing 10% FBS, antibiotics and 1 mg/ml of G418 (GIBCO Life Technologies, Burlington, ON). The G418 containing medium was replaced every 3 days. G418-resistant colonies were trypsinized and pooled for further analysis. The expression of PCP-1 and PCP-2 peptides was tested by analyzing mRNA expression using RNase protection assays as described by Peri et al. (Peri, K. G., et al., *J. Biol. chem.*, 270: 24615–24620, 1995). More particularly, total RNA was isolated using acid phenol guanidine isothiocyanate method (Chomczynski and Sacchi, 1987). Aliquots of total RNA (10 µg) were mixed with $5\times10^5$ cpm of [$^{32}$P]-labelled cRNA probes (synthesized from pIL3 and pIL4 plasmids which are expression plasmids encoding PCP-1 and PCP-2 peptides, using a commercial in vitro transcription kit sold by Promega, Madison, Wis.) in a solution containing 80% (v/v) formamide, 40 mM PIPES, pH 6.8 and 0.4 M NaCl and incubated overnight at 50° C. On the next day, the hybrids were digests with RNase A (10 µg/ml) and RNase $T_1$ (250 U/ml) in a solution containing 10 mM Tris-HCl, pH7.5, 1 mM EDTA and 0.3 M NaCl for 30 min. at 25° C. Proteinase K (10 µg) and sarcosyl (1%) were added and the incubation continued for another 30 min. at 37° C. The precipitation of RNA hybrids and resolution of labelled RNAs on urea-polyacrylamide gels were done exactly as described by Peri et al. (Peri, K. G., et al., *J. Biol. chem.*, 270: 24615–24620, 1995).

Phosphoinositide hydrolysis

The cells in 6-well dishes ($5\times10^5$/well) were incubated with [3H]-myo inositol (1 µCi/ml of 10 Ci/mmol specific activity: Amersham Canada, Mississauga, ON) for 24 hours in DMEM containing 5% FBS and antibiotics to label the inositol phospholipids. The cells were washed with DMEM containing 50 mM LiCl twice and incubated in the same medium for 15 min.

Then the cells were stimulated with 1 $\mu$M of $PGF_{2\beta}$ or $PGE_2$ for 30 min. The cells were washed with phosphate-buffered saline (PBS) once and the reactions were stopped by adding 0.4 ml of ice-cold methanol. The cells were scraped, collected into 1.5 ml microfuge tubes, 0.4 ml of water and 0.4 ml of chloroform were added, vortexed vigorously for 30 sec. and centrifuged at 14,000×g for 10 min. The aqueous layer was applied to Dowex™ AG1-X8 (formate form) ion-exchange columns (Bio-Rad, Mississauga, ON). The inositol phosphates were eluted with increasing concentrations of ammonium formate in 0.1 M formic acid exactly as described by Berridge et al.

Introduction of peptides into cells

The saponin treatment of cells on ice with peptides were conducted exactly as described by Johnson et al. (Johnson, J. A., et al., *Circ. Res.*, 79: 10086–1099, 1996). Briefly, the media from cells (at 80% confluence) in 6-well dishes was removed and saved. The cells were treated with 2 ml of room temperature PBS for 2 min. followed by ice-cold PBS for an additional 2 min. on ice. The cells were then incubated for 10 min. in 2 ml of freshly prepared permeabilization buffer (20 mM HEPES, pH 7.4, 10 mM EGTA, 140 mM KCl, 50 $\mu$g/ml saponin, 6 mM ATP and 5 mM oxalic acid) containing varying concentrations of peptides, PCP-3 and PCP-4. The cells were washed gently four times on ice with 2 ml of ice-cold PBS each time. The cells were incubated for 20 min. in the fifth wash on ice. The cells were then successively incubated for 2 min. with 2 ml of PBS at room temperature and at 37° C. The conditioned media was returned to the cells and they were allowed to recover for 30 min. before determining phosphoinositide hydrolysis in response to prostaglandins.

Discussion

In accordance with the present invention, a novel strategy of utilizing intracellular interface between the FP receptor and the $G_{\alpha q}$-protein as a target for designing inhibitors of FP receptor function was used. This method can be generalized to all G-protein-coupled receptors. Peptides derived from the intracellular domains of FP receptors (PCP-1 and PCP-2) and the $\alpha$N and $\alpha$C helices of Gq-protein (PCP-3 and PCP-4 respectively) were found to be effective inhibitors of FP receptor.

The present invention will be more readily understood by referring to the following examples which are given to illustrate the invention rather than to limit its scope.

EXAMPLE I

Effects of intracellular expression of PCP-1 and PCP-2 peptides on FP receptor function Cell lines expressing the peptides, PCP-1 and PCP-2, were stimulated with 1 $\mu$M $PGF_{2\alpha}$ and $PGE_2$ for 30 min. and the inositol phosphates were measured by anion exchange chromatography as described by Berridge et al. (Berridge, M. J., et al., *Biochem. J.*, 212: 473–482, 1983) Briefly, the medium was discarded and the inositol triphosphate (IP3) synthesis was stopped by adding 0.6 ml ice-cold methanol. The cells were scraped and collected into polypropylene tubes. Distilled water (0.5 ml) and chloroform (0.6 ml) were added and vigorously vortexed for 2 min. The phases were separated by centrifugation at 6000×g for 10 min. The aqueous phase was applied to AG-1X-8 (Formate form) anion exchange columns (1 ml bed volume) and free inositol was eluted with 10 ml of water, followed by 60 mM ammonium formate in 0.1 M formic acid. Then, the inositol phosphates were eluted with 5 ml of 1.2 M ammonium formate in 0.1 M formic acid. After adding 3 volumes of scintillation cocktail (Optiphase-HiSafe III™), the eluates were counted by scintillation spectrophotometry.

Figure 1B:
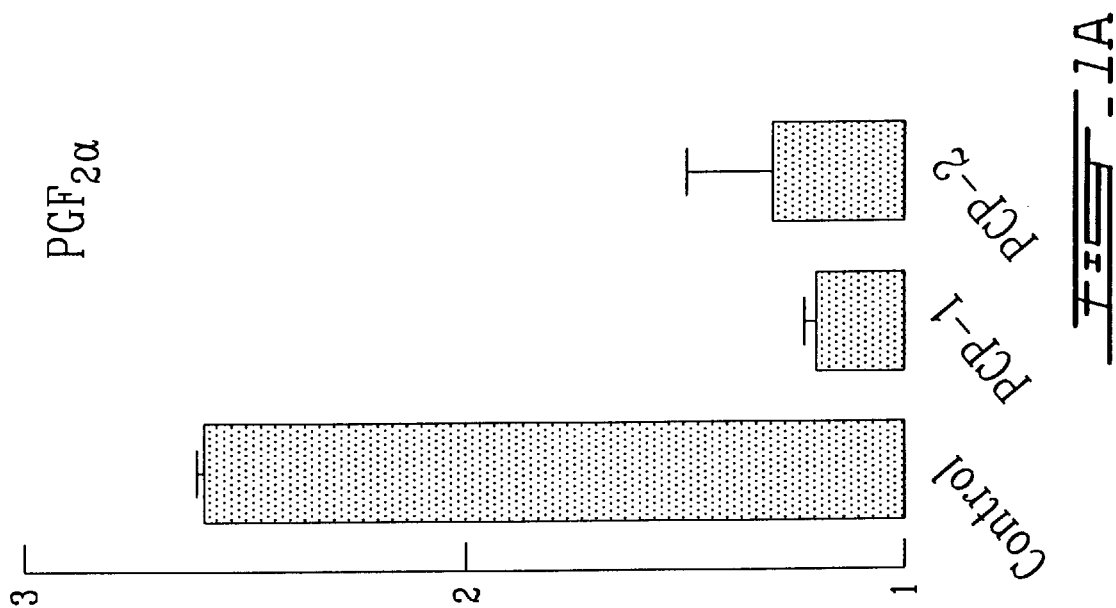

As shown in FIG. 1A, expression of either PCP-1 or PCP-2 inhibited ligand-stimulated phosphoinositide hydrolysis (n=3). Both PCP-1 and PCP-2 were stably expressed intracellularly. The cells were labelled with $^3$H-myo inositol for 24 hours and stimulated with 1 $\mu$M of $PGF_{2\alpha}$ or $PGE_2$ for 30 min. Inositol phosphates were separated by ion exchange chromatography and determined by scintillation counting. Data are expressed as fold stimulation in phosphoinositide hydrolysis over unstimulated controls. On the other hand, stimulation of a related prostaglandin receptor expressed in these cells (with which FP receptor shows highest sequence identity among all G-protein coupled receptors), EP1, with $PGE_2$ did not affect inositol phosphate generation by this receptor (FIG. 1B). Both EP1 and FP receptor are coupled to Gq-class of G-proteins and generate inositol phosphates upon stimulation with ligands. The inhibition of FP receptor by ectopically expressed PCP-1 and PCP-2 peptides is specific and these peptides will be modified to produce smaller and more diffusible inhibitors of FP function.

EXAMPLE II

Effects of PCP-3 and PCP-4 peptides of human Gq protein on FP receptor function

Figure 2B:
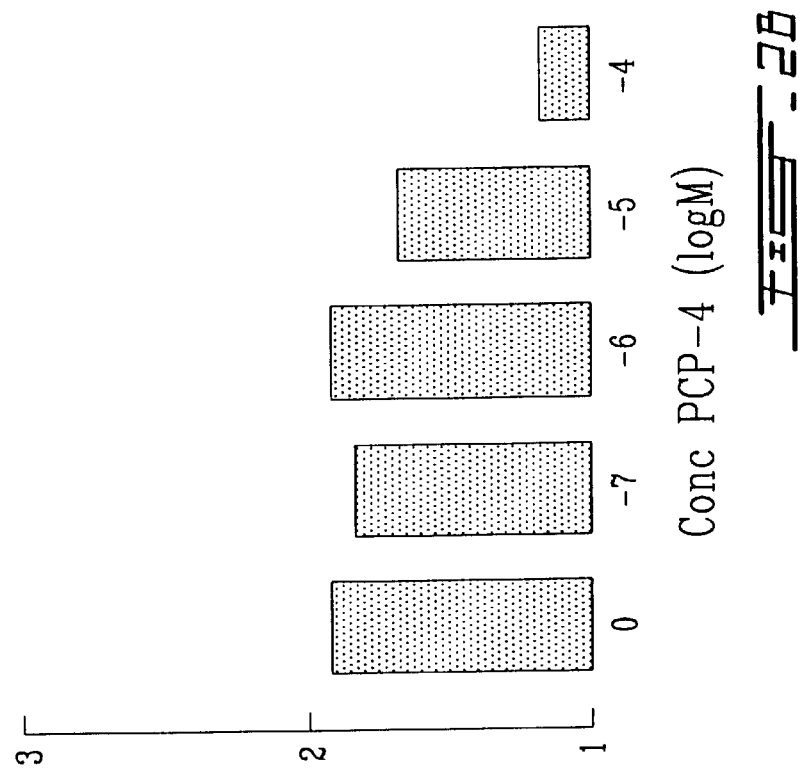
FIG. 2B illustrates a dose-response of PCP-4 on $PGF_{2\alpha}$ receptor function.
Figure 2A:
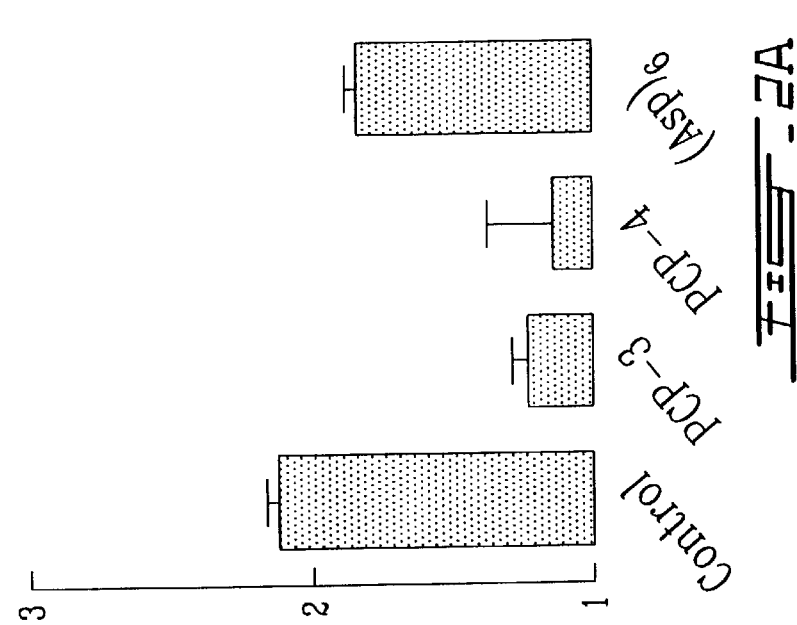
FIG. 2A illustrates the effects of $G_{\alpha q}$-derived peptides on FP receptor function.

The second component of interaction between the FP receptor and G-protein is the domain of Gq which is composed of $\alpha$N and $\alpha$C helices (Lambright, D. G., et al., *Nature*, 379: 311–319, 1996). Peptides CLSEEAKEAR RINDEIERQL RRDKRDARRE-NH$_2$ (PCP-3) and KDTILQLNLK EYNLV-NH$_2$ (PCP-4), corresponding to $\alpha$N and $\alpha$C helices, respectively, were chemically synthesized using F moc chemistry and introduced transiently into permeabilized A549 cells. The cells were stimulated with $PGF_{2\alpha}$, as described above and inositol phosphate synthesis was measured. The results are expressed as fold stimulation of phosphoinositide hydrolysis by the ligand (n=3). Both $\alpha$N and $\alpha$C helical peptides of Gq protein inhibited agonist-induced activation of FP receptor, whereas a control peptide (poly aspartic acid, Asp6) did not affect the receptor function (FIG. 2A). PCP-3 and PCP-4, at 100 $\mu$M, were introduced into $^3$H-myo inositol-labelled permeabilized A549 cells and stimulated with 1M $PGF_{2\alpha}$ for 30 min. Inositol phosphates were separated by ion exchange chromatography and determined by scintillation counting. A dose-response of $\alpha$C peptide on FP receptor revealed a half maximal inhibitory concentration of 50 $\mu$M of peptide under these conditions (FIG. 2B). In FIG. 2B, data are expressed as fold-stimulation by $PGF_{2\alpha}$ over control cells not treated with peptide.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An antagonist of a G-protein-coupled receptor which binds to an intracellular molecular interface between the receptor and a $G_{60\ q}$-protein, wherein said antagonist selected from a group consisting of RVKFKSQQHRQGRSHHLEM (SEQ ID No:3); RKAVLKNLYKLASQCCGVHVISLHIWELSSIKNSLLKVAAISESPVAEKSAST (SEQ ID:4); CLSEEAKEARRINDEIERQLRRDKRDARRE-$NH_2$ (SEQ ID:9), and
KDTILQLNLKEYNLV-$NH_2$ (SEQ ID: 10), wherein said antagonist when bound to the intracellular molecular interface is hampering signal transduction from said receptor.

2. The antagonist of claim 1, wherein the receptor is the $PGF_{2\alpha}$ receptor of prostaglandin.